United States Patent
Vaz

(10) Patent No.: US 9,977,872 B2
(45) Date of Patent: May 22, 2018

(54) DISPENSING SYSTEM FOR PHARMACIES

(71) Applicant: Innotech Resources Pte Ltd, Singapore (SG)

(72) Inventor: Ashley John Vaz, Singapore (SG)

(73) Assignee: INNOTECH RESOURCES PTE LTD, Singapore (SG)

(*) Notice: Subject to any disclaimer, the term of this patent is extended or adjusted under 35 U.S.C. 154(b) by 0 days. days.

(21) Appl. No.: 14/879,205

(22) Filed: Oct. 9, 2015

(65) Prior Publication Data
US 2016/0132659 A1 May 12, 2016

(30) Foreign Application Priority Data

Oct. 9, 2014 (SG) .......................... 10201406490W

(51) Int. Cl.
G06F 19/00 (2018.01)
G05B 15/02 (2006.01)
G07F 17/00 (2006.01)

(52) U.S. Cl.
CPC ......... G06F 19/3462 (2013.01); G05B 15/02 (2013.01); G07F 17/0092 (2013.01)

(58) Field of Classification Search
None
See application file for complete search history.

(56) References Cited

U.S. PATENT DOCUMENTS 6,338,007 B1* 1/2002 Broadfield ........... A61G 12/001
221/123
7,840,307 B2 11/2010 Mauger et al.
8,355,962 B2* 1/2013 Delaney ............... G06Q 10/087
340/10.1
8,380,346 B2* 2/2013 Chudy ................ G06F 19/3462
221/6
2003/0105552 A1* 6/2003 Lunak ...................... B65G 1/12
700/214
2005/0027601 A1* 2/2005 Walker ................. G06Q 10/087
705/15

(Continued)

OTHER PUBLICATIONS

Newsletter entitled "Award Winning SGH Pharmacy System Uses Latest Manufacturing and RFID Technologies to Shorten Waiting Times, Increase Staff Productivity" https://www.ihis.com.sg/MediaCentre/mr/Pages/Award-Winning-SGH-Pharmacy-System-Uses-Latest-Manufacturing-and-RFIO-Technologies-To-Short . . . Mar. 13, 2014.

(Continued)

Primary Examiner — Gene O Crawford
Assistant Examiner — Stephen L Akridge
(74) Attorney, Agent, or Firm — King & Schickli, PLLC

(57) ABSTRACT

There is disclosed a dispensing system for pharmaceutical products, the dispensing system comprising: a plurality of individually lockable storage bins for storing respective pharmaceutical products, each storage bin comprising a lock coupled to an actuator; a database which associates respective bin identifiers with respective product codes of the pharmaceutical products; and a dispensing server comprising a dispensing module which is configured to: receive a selection of one of said pharmaceutical products; receive scan data indicative of a product code for the selected product; determine, from said database, a bin identifier associated with the product code; and send an unlock signal to the actuator of a storage bin corresponding to said bin identifier.

10 Claims, 4 Drawing Sheets

(56) References Cited

U.S. PATENT DOCUMENTS

| | | | | |
|---|---|---|---|---|
| 2006/0020366 | A1* | 1/2006 | Bloom | B07C 3/00 700/226 |
| 2006/0124743 | A1* | 6/2006 | Venema | G06Q 10/087 235/462.01 |
| 2008/0288105 | A1* | 11/2008 | Mauger | G07F 11/62 700/231 |
| 2012/0150340 | A1* | 6/2012 | Suess | B65G 1/137 700/216 |
| 2012/0232692 | A1* | 9/2012 | Liu | G06F 19/327 700/236 |
| 2013/0332271 | A1* | 12/2013 | Hay | G06O 20/20 705/14.51 |
| 2014/0172159 | A1* | 6/2014 | Unmussig | G07F 7/06 700/232 |
| 2015/0081088 | A1* | 3/2015 | Lyon | G06Q 10/0875 700/216 |

OTHER PUBLICATIONS

Media Release entitled "SGH Pharmacy uses RFID technology and automated system to enhance medication safety and improve operational efficiency" Aug. 14, 2013 Singapore General Hospital SingHealth.

* cited by examiner

DISPENSING SYSTEM FOR PHARMACIES

TECHNICAL FIELD

The present invention relates to a dispensing system for pharmaceutical products, and is particularly useful for outpatient pharmacies.

BACKGROUND

Typically, pharmacies store and dispense thousands of prescription drugs manually. Packaged drugs are generally stored in storage bins on gondola shelving. It is not uncommon for there to be human error during manual picking of drug packages from the storage bins, possibly leading to the wrong drug and/or the wrong quantity of drug being picked and dispensed to patients. This has on occasion led to serious complications for, and even death of, patients receiving the wrong dose and/or drug.

There remains a need for a dispensing system which can minimize the occurrence of erroneous picking and dispensing of drugs.

SUMMARY

In a first aspect of the present invention, there is provided a dispensing system for pharmaceutical products, the dispensing system comprising:
  a plurality of individually lockable storage bins for storing respective pharmaceutical products, each storage bin comprising a lock coupled to an actuator;
  a database which associates respective bin identifiers with respective product codes of the pharmaceutical products; and
  a dispensing server comprising a dispensing module which is configured to:
    receive a selection of one of said pharmaceutical products;
    receive first scan data indicative of a product code for the selected product;
    determine, from said database, a bin identifier associated with the product code;
    receive second scan data indicative of a scanned bin identifier of a storage bin; and
    if the scanned bin identifier matches the bin identifier associated with the product code, send an unlock signal to the actuator of the storage bin corresponding to said scanned bin identifier.

By requiring receipt of the first and second scan data, and subsequent matching of the scanned bin identifier with the correct bin identifier associated with the scanned product code prior to unlocking of the bin, it is possible to ensure that the product selected for dispensing or replenishment matches the product which is actually stored or intended to be stored in the scanned bin.

In another aspect, the present invention provides a method of controlling access to pharmaceutical products, the method comprising:
  providing a plurality of individually lockable storage bins for storing respective ones of the pharmaceutical products, each storage bin comprising a lock coupled to an actuator;
  providing a database which associates respective bin identifiers with respective product codes of the pharmaceutical products; and
  providing a dispensing module which is configured to:
    receive a selection of one of said pharmaceutical products;
    receive first scan data indicative of a product code for the selected product;
    determine, from said database, a bin identifier associated with the product code;
    receive second scan data indicative of a scanned bin identifier of a storage bin; and
    if the scanned bin identifier matches the bin identifier associated with the product code, send an unlock signal to the actuator of the storage bin corresponding to said scanned bin identifier.

BRIEF DESCRIPTION OF THE DRAWINGS

Embodiments of the invention will now be described, by way of non-limiting example only, with reference to the accompanying drawings in which.

DETAILED DESCRIPTION OF EMBODIMENTS

Embodiments of the present invention provide software, locking mechanisms, light guided pick systems and individually lockable storage bins designed to meet cabinet dimensions to suit a typical floor layout of an outpatient pharmacy. In some embodiments, the lockable storage bins may be provided in modular form for incorporation into existing outpatient pharmacy manual shelves and gondola systems. However, it will be appreciated that the present invention may be readily adapted to other settings in which it is desired to control access to prescription medication, and to ensure that the medication is accurately dispensed and stocked.

Figure 1:
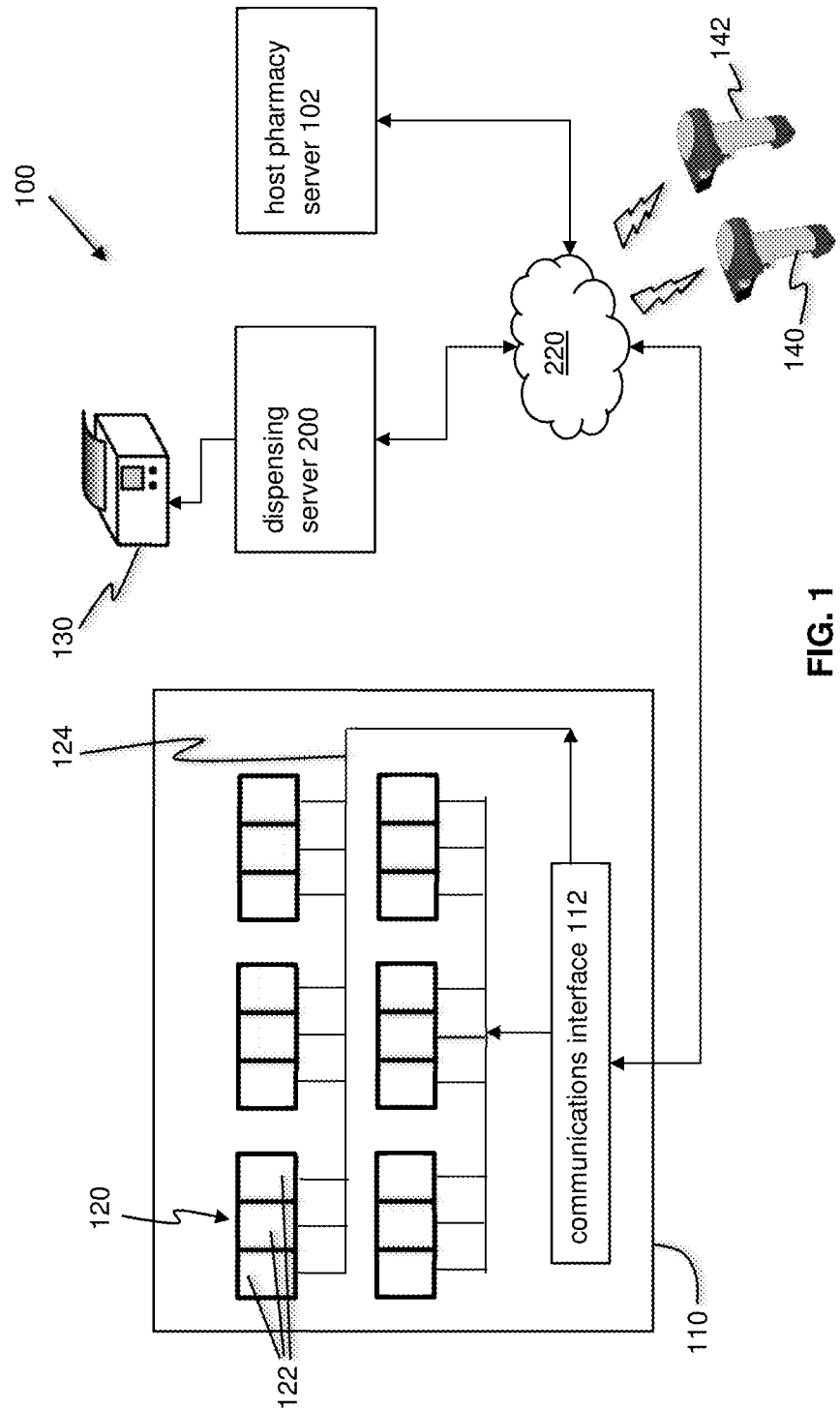
FIG. 1 is a block diagram of a pharmaceutical dispensing system according to embodiments of the invention.

Referring initially to FIG. 1, there is shown in highly schematic form a dispensing system 100 comprising a dispensing server 200 and a shelving system 110, such as a gondola shelving system typically used in outpatient pharmacies, within which there is provided a plurality of individually lockable storage bins 122. The storage bins 122 may, but are not necessarily, arranged in modules 120 of three bins. The modules 120 may contain fewer or more bins depending on the bin size, and the width of the recess that they are to be stored in.

Each module 120 is connected via cabling 424 to a communications line 124 which communicatively couples the module 120 to a communications interface 112. The communications interface 112 allows communication between the dispensing server 200 and the individual bins 122 of module 120, via network 220, to operate actuators of respective locks of the bins 122 and LED units (not shown) of the bins 122. The network 220 may be a wide area network such as the Internet, or a local area network, for example.

Dispensing server 200 is also in communication with a host pharmacy system 102 via network 220. The host pharmacy system 102 sends prescription data to the dispensing server 200 to queue pharmaceutical products for dispensing from the bins 122. The dispensing server 200 is connected to a label printer 130 for printing barcode labels corresponding to products queued by the host pharmacy system 102, and selected by a user of dispensing server 200 for picking from bins 122.

Figure 2:
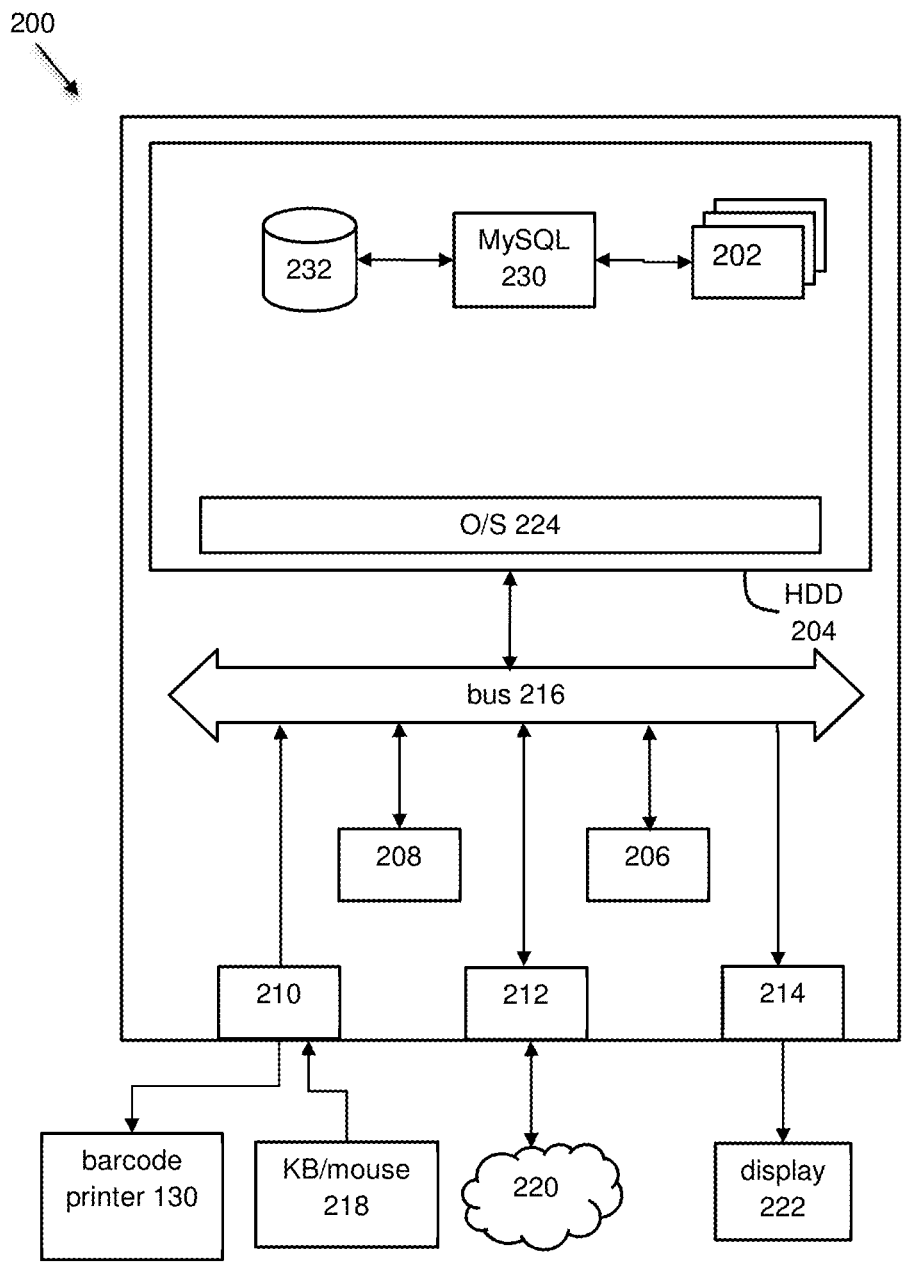
FIG. 2 is a block diagram of a dispensing server of the system of FIG. 1.

The dispensing server 200 is shown in more detail in FIG. 2. In the described embodiment, the dispensing server is a standard computer system such as an Intel IA-32 based computer system 200, and the associated processes executed by the system 200 are implemented in the form of programming instructions of one or more software modules or components 202 (such as a dispensing module, described in more detail below) stored on tangible and non-volatile (e.g., solid-state or hard disk) storage 204 associated with the computer system 200, as shown in FIG. 2. However, it will be apparent that the processes could alternatively be implemented, either in part or in their entirety, in the form of one or more dedicated hardware components, such as application-specific integrated circuits (ASICs), and/or in the form of configuration data for configurable hardware components such as field programmable gate arrays (FPGAs), for example.

As shown in FIG. 2, the system 200 includes standard computer components, including random access memory (RAM) 206, at least one processor 208, and external interfaces 210, 212, 214, all interconnected by a bus 216. The external interfaces include universal serial bus (USB) interfaces 210, at least one of which is connected to a keyboard 218 and pointing device such as a mouse, and one of which is connected to the label printer 130, and a network interface connector (NIC) 212 which connects the system 200 to a communications network 220 such as the Internet, via which the prescription data can be accessed by the system 200.

The system 200 also includes a display adapter 214, which is connected to a display device such as an LCD panel display 222, and a number of standard software modules, including an operating system 224 such as Linux or Microsoft Windows. The system 200 may include structured query language (SQL) support 230 such as MySQL, available from http://www.mysql.com, which allows data to be stored in and retrieved from an SQL database 232. The SQL database 232 includes data representing associations between identifiers of the bins 122 and product codes of pharmaceutical products which are stored or intended to be stored in bins 122.

In some embodiments, the dispensing system may comprise more than one computer system. For example, in one embodiment, the dispensing system may comprise a first computer system 200 which communicates with host pharmacy system 102 to receive prescription data, and which stores pharmaceutical product and bin details in database 232 as described above. The dispensing system may further comprise a second computer system (not shown) which interfaces with the communication interface 112 of the gondola system in order to actuate the mechanical and electrical components of the bins 122. Thus, the data processing functions are controlled by the first computer system 200 while the mechanical/electrical control functions are controlled by the second computer system.

Typically, the gondola system 110 may contain 100 to 250 bins 122, but is not limited to any particular number of bins 122 or modules 120. Additionally, while only one gondola is shown in FIG. 1, it will be appreciated that multiple gondolas may form part of the gondola system 110 and each be in communication with dispensing server 200.

Figure 3:
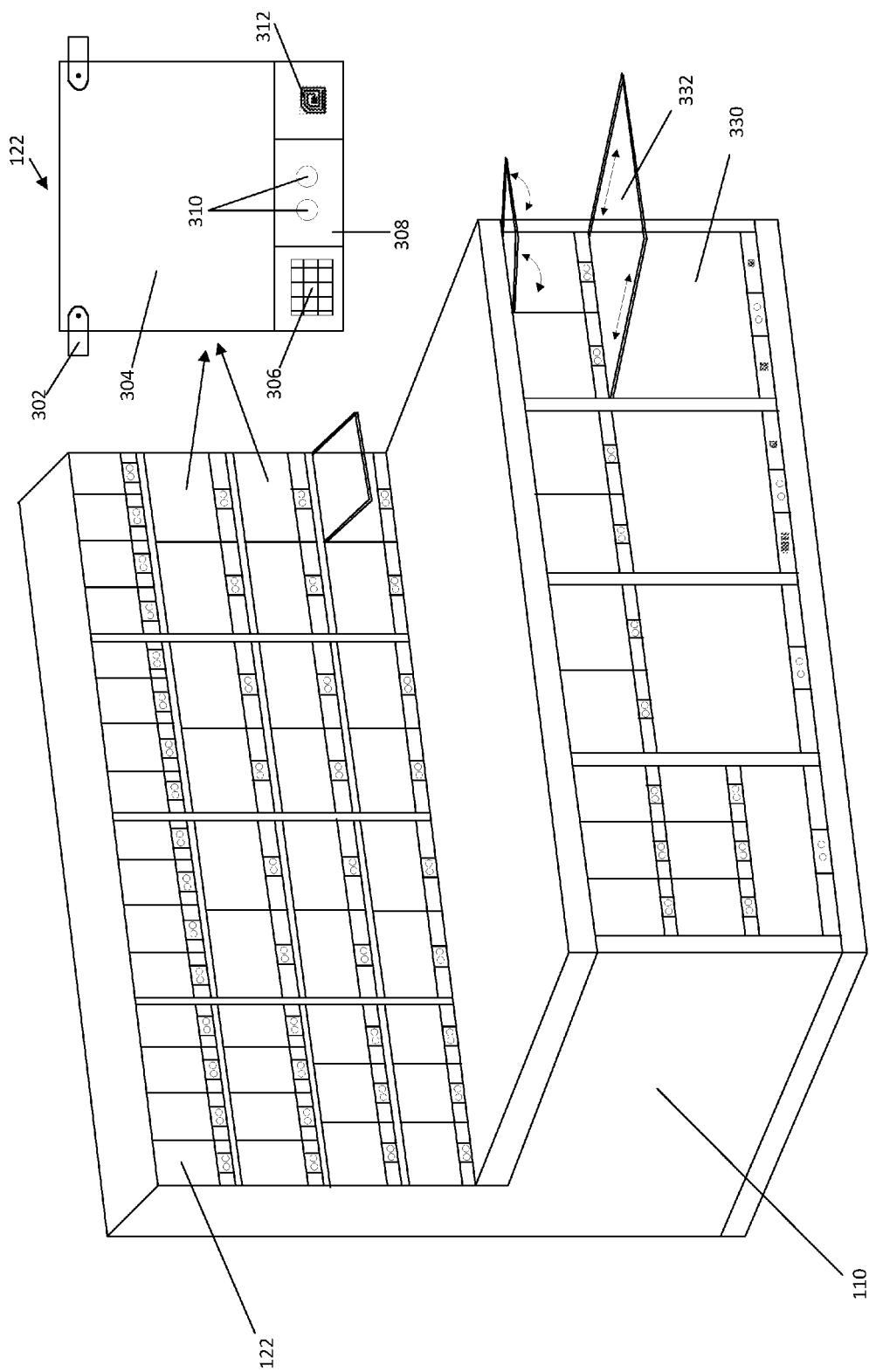
FIG. 3 is a schematic drawing of a gondola shelving unit of the system of FIG. 1.

Turning to FIG. 3, one exemplary configuration of gondola 110 is shown. The gondola 110 may contain bins 122 as shown in FIG. 1, and may also contain differently sized bins, such as large bins 330 which can be used for bulk storage of products. Large bins 330 may have respective doors 332 which can slide into a recess of the gondola 110 to allow easier access to their contents.

One exemplary bin 122 is shown in detail at the top right of FIG. 3. The bin 122 has hinges 302 about which a clear door 304 can swing to allow access to the contents of the bin 122. The bin 122 has a remotely actuatable locking mechanism 308. Locking mechanism 308 comprises a lock, an actuator for the lock, and a cable for coupling the actuator to the communications interface 112, such that the actuator can receive lock and unlock signals from the dispensing server 200 at the appropriate times.

The bin 122 also has visual indicators in the form of LED units 310. The LED units 310 are also coupled to the communications interface 112 such that dispensing server 200 can send signals to the LED units 310 to switch them on or off, or to cause them to blink on and off, depending on the action that is required of a picker dispensing products from or restocking products into the bin 122.

Each bin 122 has a machine-readable bin label 306 in the form of a barcode or QR code which contains information relating to an identifier of the bin. The barcode or QR code can be scanned by a suitable barcode reader 140 (FIG. 1) which then transmits, via network 220, the scanned bin identifier to the dispensing server 200. The bin 122 may also have a second machine-readable bin label 312 in the form of an RFID tag, which is readable by an RFID scanner 142 (FIG. 1), which again can transmit the bin identifier to the dispensing server 200. Either one or both of the labels 306, 312 may be scanned as part of a picking or replenishing process. Requiring both to be scanned adds an extra level of authentication, thus ensuring greater accuracy.

In addition to the machine-readable labels 306, 312 of the bin 122, the products stored within the bin 122 each have a machine-readable product label, such as a barcode, QR code or RFID tag, which when scanned by a suitable reader such as reader 140 or reader 142, transmits a product code corresponding to the product label to the dispensing server 200. A dispensing module 202 of the dispensing server 200 determines (using database 232) which bin corresponds to the scanned product code. If the bin thus identified matches the scanned bin identifier, the dispensing module 202 sends an unlock signal to the actuator of the bin 122 to allow the bin to be opened.

Figure 4:
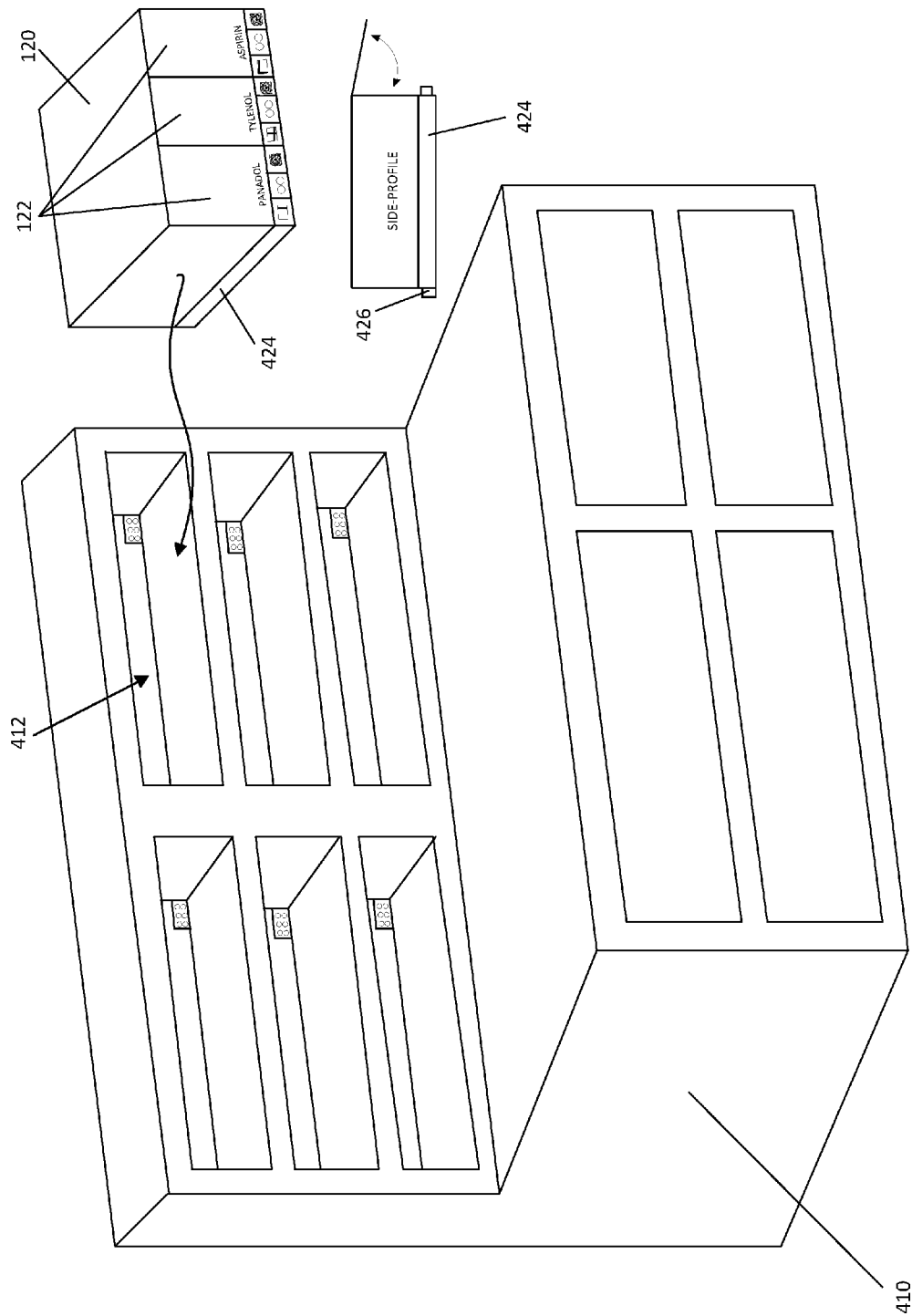
FIG. 4 is a schematic drawing of an alternative gondola shelving unit of the system of FIG. 1.

An alternative gondola 410 is shown in FIG. 4. In FIG. 4, the gondola 410 is a conventional pharmacy gondola which has been retrofitted with modules 120 of bins 122. Each recess 412 of the gondola 410 may contain one of the modules 120, for example. Each module 120 has a base section 424 containing cabling to provide power to the LEDs and locking mechanism, and connectivity to communications interface 112. The base section 424 has a controller socket 426 which plugs into a mating controller socket 414 located in the recess 412 to provide connectivity between the modular gondola 410 and the dispensing server 200.

In one example of a dispensing process, a user selects, at dispensing server 200, a product (for example, one of the queued products indicated by the prescription data sent by the host pharmacy server 102). The dispensing server 200 prints a barcoded label for the product using label printer 130. Next, a picker scans the barcoded label using barcode reader 140. The scanned product code from the barcoded label is received by dispensing module 202, which queries the database 232 to determine which bin or bins contain the corresponding product. The dispensing module 202 then causes one or both of the LEDs of each identified bin 122 to be switched on to visually identify the bin(s) to the picker.

In particular, the LEDs can be operated in "blink" mode, whereby they flash on and off continually. The dispensing module 202 also sends an unlock signal to the identified bin(s). The picker can then retrieve products from the unlocked bins. Since only the bins corresponding to the selected product will be unlocked, accuracy of dispensing is assured. In one variation, the dispensing module 202 may require an extra level of authentication, by requiring that the picker scan barcode label 306 and/or RFID tag 312 of the identified bin 122, and cross-checking the scanned bin identifier against the previously determined bin identifier, before sending the unlock signal.

Next, the picker scans the barcode of each label of each drug package which is dispensed from the unlocked bin. The dispensing module 202 receives the scan data corresponding to the product codes of the scanned labels, and checks the received product codes against the product and quantity previously selected by the user. Once the correct quantity has been scanned, the dispensing module 202 causes the LED to stop flashing to provide a visual cue to the picker that the prescription is complete. The door is then closed, the user provides input verifying the quantity at dispensing server 200, and dispensing module 202 sends a lock signal to the bin.

The system 100 may be suitable for use with any number of different types of drug packaging, such as Blisters, Boxes, Bottles, Vials, Strips, Flexi-packages, etc., but is not limited to such packages or retail packages. Essentially any type of packaging can be used provided it is capable of carrying a machine-readable identification element such as a barcode, QR code, RFID tag, etc.

The bins 122 may have different coloured LEDs from each other, so that multiple pickers can be manually picking from the gondola 110 at the same time. The different colours provide a visual indication to the different pickers as to which bins they are allowed to pick from. The barcode readers 140 used by the pickers may be associated in the database 232 with a particular colour, so that for example, if the picker assigned "green" tries to scan a bin which is flashing red, the dispensing module 202 will determine that the picker is not allowed to access that bin, and will not send an unlock signal.

In an example of a replenishment process, a user at dispensing server 200 may scan barcode labels of packages of products to be replenished. The dispensing module 202 receives the corresponding scanned product codes and queries database 232 to determine which bin(s) the products should be stored in. For each identified bin, the dispensing module 202 causes the LED unit of the bin to flash on and off continuously to indicate to the picker which bin to store the product in. The colour may be unique to the picker, as before. The picker then scans the barcode label 306 of the visually indicated bin, to send the bin identifier to the dispensing server 200. If the dispensing module 202 determines that the scanned bin identifier matches the previously determined bin identifier corresponding to the scanned product code, the dispensing module 202 sends an unlock signal to the actuator of the bin, such that the picker can open the bin to put the products inside. Once replenishment is complete, the door of the bin is closed, and the user at dispensing server 200 enters the quantity and/or scans the product labels to confirm the quantity added, and may also key in expiration date and lot number, and then confirm the replenishment quantity. Once confirmed, the dispensing module 202 switches off the LED of the bin, and sends a lock signal to the actuator of the bin lock.

In one embodiment, a dispensing process involves the following steps:

When the server 200 receives a prescription order:
1. Picker selects RX line item:
2. System Checks the drug master database 232
3. Checks location & Bin ID
4. Checks inventory & available stock
5. Barcode Printer prints 'Patient RX Drug Label w barcode'.
6. Picked scans the 'Patient RX Drug Label barcode'.
7. System Lights up LED identifier 310 (to attract attention to the Smartbin). This can be initiated by selecting the RX Line item on the system GUI menu system &/or Scanning the Patient Rx Drug Label Barcode.
8. The Correct Picker Validation (Optional: Verify correct picker by scanning Staff ID Tag)
9. Picker goes to flashing Bin
10. Scans the Bin ID 306, 312 (Barcode/RFID Tag)
11. When the correct picker (optional) and RX Drug Label Barcode and SmartBin ID is 'matched', Only then will the Smartbin 122 'unlock'.

In one embodiment, a replenishment process involves the following steps:
1. The Drug name & Drug code is selected at server 200
2. System Checks Location
3. System Checks Inventory
4. Confirm correct drug name in database 232
5. Scan Manufacturers Drug Packaging Barcode (Consistent with Drug Setup in Database 232)
6. Smartbin to Flash the LED 310
7. Scan the Pharmacist Staff ID Tag (Verify Authorized Pharmacist)
8. Scan the Smartbin ID number for match
9. If Authorized Pharmacist+Manufacturers Drug Package Barcode+Correct Smartbin ID match; Only then, will the Smartbin 122 'Unlock'.
10. Quantity is entered, confirmed by yet pharmacist (May require 2 Pharmacists to confirm/validate restocking).
11. Physical Stock put in the SmartBin and confirmed in the system GUI
12. SmartBin is then Locked Embodiments of the invention may also relate to the following:

A. Locking SmartBins

Locking SmartBins strengthen your pharmacy's drug accountability by helping to prevent drug picking and replenishment errors. They improve inventory control by ensuring that the SmartBin remains locked until the appropriate steps are established in the inventory procedures. The PSGS system recognizes each SmartBin location by its SmartBin Barcode. For each SmartBin setup; the SmartBin Barcode is associated to a Drug name, Drug Code and Drug Barcode.

Used together with PSGS auditing and security features, remote locking SmartBins help secure your pharmacy by restricting picking & replenishment activities to authorized pharmacy personnel only.

B. Locating SmartBins

The PSGS maintains a dynamic database of all SmartBins and Drugs that have been set up for dispensing and tracks which SmartBins currently house these drugs. Users need to easily identify and locate any physical SmartBin on the gondola.

Each SmartBin is identified by a Location ID, Barcode (&/or RFID) and an LED light.

C. Ultra Bright LED Light Guided Picking Verified by Barcode

To help minimize picking errors, when a prescription is queued by the HOST Pharmacy IT system, the prescription is selected and initiated by the authorized user logged in. The line item is selected and a prescription Drug Label is printed by the barcode printer.

The user scans the printed prescription Drug Label barcode with a barcode reader, the LED light at the SmartBin location will flash on & off continuously and unlock. Each drug in the SmartBin is labelled with a barcode.

Note: The Barcode on each SmartBin may be enhanced with an RFID Tag; enhancing reading, with either or/Both required.

The user scans the barcode of each drug label when withdrawn from the SmartBin. (Eg. RX quantity is 5 strips; Scan the drug label on each of the 5 strips) Upon scanning the correct number (Qty) of labels and the RX quantity is fulfilled; The LED Light stops flashing. This helps ensure correct drug and correct quantity.

When picking is complete, the user closes the door, verifies the quantity on the console, confirms the picked quantity and the SmartBin door is locked.

The next line item is selected and the process repeats, until the prescription is completed.

D. 6 Color Light Guided Replenishment Verified by Barcode

To help minimize opportunities for error, the authorized user scans the Drug Package Label associated with the Drug setup for the SmartBin. The LED on the corresponding SmartBin flashes.

The color of LED light guides the picker to the correct SmartBin and the color is unique to the picker.

Note: The system can support a single color LED Light or up to 6 colors LED Lights. More LED colors assigned to pickers, translates to more independent pickers with unique colors for simultaneous picking.

The user then uses a barcode scanner to scan the barcode of the lighted SmartBin. Upon a matched verification of the Drug item and the SmartBin barcode; The locked SmartBin will then unlock the clear acrylic door for easy visual verification of drug, prior to loading of the drugs.

When restocking is complete, the user closes the door, enters the quantity &/or scans each drug item label to confirm quantity added, key in expiration date, lot number, then reconfirms the replenishment quantity. The SmartBin stops flashing and the door is locked.

The next drug packaging barcode is scanned and the process repeats, until replenishment is completed.

Likewise, when you initiate a 'Return-to-Stock' procedure, scanning the prescription Drug Label displays the SmartBin location ID and flashes the SmartBin's LED indicator.

E. Audit Functions

For pharmacies that want to control which employees may replenish drugs in SmartBins, PSGS offers an auditing option that allows super-users to set tasks and manage authorized personnel.

When this option is enabled, authorized users will be required to scan the barcode on their Staff ID to unlock the SmartBin for replenishment. Unauthorized users will not be able to initiate replenishment tasks.

F. Local Reports At Gondolas

The following reports shall be made available by each Gondola:
1. PSGS Gondola Master Drug List
2. PSGS Gondola Inventory Status
3. User Activity by defined date range
4. SmartBin Activity by defined date range
5. Low Inventory SmartBins—Below Trigger Levels
*Not limited to these reports

The invention claimed is:

1. A dispensing system for pharmaceutical products, the dispensing system comprising:
a plurality of individually lockable storage bins for storing respective pharmaceutical products, each storage bin comprising a lock coupled to an actuator and at least one visual indicator device;
a database which associates respective bin identifiers with respective product codes of the pharmaceutical products;
a plurality of scanning devices, each having a scanner identifier, respective scanner identifiers being associated with respective colors of the at least one visual indicator device; and
a dispensing server comprising a dispensing module which is configured to:
receive a selection of one of said pharmaceutical products;
receive first scan data indicative of a product code for the selected product;
determine, from said database, a bin identifier associated with the product code;
receive second scan data indicative of a scanned bin identifier of a storage bin; and
if the scanned bin identifier matches the bin identifier associated with the product code, send an unlock signal to the actuator of the storage bin corresponding to said scanned bin identifier, and an actuation signal to change a visual appearance of the at least one visual indicator device of the storage bin corresponding to said bin identifier, allowing a user having used at least one of the plurality of scanning devices to identify respective colors of the at least one visual indicator device associated with respective scanner identifiers to retrieve the selected product from the storage bin.

2. A dispensing system according to claim 1, wherein the plurality of storage bins is arranged in, or is configured to be arranged in, a gondola display.

3. A dispensing system according to claim 1, wherein the at least one visual indicator device is a light emitting diode (LED).

4. A dispensing system according to claim 1, wherein the storage bins are arranged in groups each associated with a group identifier in said database, and wherein respective group identifiers are associated with respective colors of the visual indicator devices.

5. A dispensing system according to claim 4, wherein the respective scanner identifiers are associated with respective group identifiers in said database.

6. A dispensing system according to claim 2, wherein the at least one visual indicator device is a light emitting diode (LED).

7. A dispensing system according to claim 2, wherein the storage bins are arranged in groups each associated with a group identifier in said database, and wherein respective group identifiers are associated with respective colors of the at least one visual indicator device.

8. A dispensing system according to claim 3, wherein the storage bins are arranged in groups each associated with a group identifier in said database, and wherein respective group identifiers are associated with respective colors of the visual indicator devices.

9. A dispensing system according to claim 1, wherein the storage bins further comprise at least one machine readable bin label chosen from a group comprising a barcode, a QR code, and an RFID tag.

10. A method of controlling access to pharmaceutical products, the method comprising:
  providing a plurality of individually lockable storage bins for storing respective ones of the pharmaceutical products, each storage bin comprising a lock coupled to an actuator and at least one visual indicator device;
  providing a database which associates respective bin identifiers with respective product codes of the pharmaceutical products;
  providing a plurality of scanning devices, each having a scanner identifier, respective scanner identifiers being associated with respective colors of the at least one visual indicator device; and
  providing a dispensing module which is configured to:
    receive a selection of one of said pharmaceutical products;
    receive first scan data indicative of a product code for the selected product;
    determine, from said database, a bin identifier associated with the product code;
    receive second scan data indicative of a scanned bin identifier of a storage bin; and
    if the scanned bin identifier matches the bin identifier associated with the product code, send an unlock signal to the actuator of the storage bin corresponding to said scanned bin identifier, and an actuation signal to change a visual appearance of the last least one visual indicator device of the storage bin corresponding to said bin identifier, allowing a user having used at least one of the plurality of scanning devices to identify respective colors of the at least one visual indicator device associated with the respective scanner identifiers to retrieve the selected product from the storage bin.

* * * * *